United States Patent [19]

Shinoki et al.

[11] Patent Number: 5,547,848

[45] Date of Patent: Aug. 20, 1996

[54] IMMUNOASSAY ELEMENT CONTAINING A PULVERIZED WATER-INSOLUBLE POLYSACCHARIDE AND PROCESS FOR IMMUNOASSAY

[75] Inventors: Hiroshi Shinoki; Toshikage Hiraoka; Masashi Ogawa, all of Saitama, Japan

[73] Assignee: Fuji Photo Film Co., Ltd., Kanagawa, Japan

[21] Appl. No.: 393,240

[22] Filed: Feb. 23, 1995

Related U.S. Application Data

[63] Continuation of Ser. No. 846,804, Mar. 4, 1992, abandoned.

[30] Foreign Application Priority Data

Mar. 4, 1991 [JP] Japan ..................................... 3-060972

[51] Int. Cl.⁶ ..................... G01N 33/535; G01N 33/548
[52] U.S. Cl. ................. 435/7.9; 435/7.92; 435/18; 435/22; 435/188; 436/514; 436/541; 436/169; 436/530; 422/56; 422/60; 422/68.1; 422/101
[58] Field of Search ..................................... 435/7.9, 7.92, 435/18, 22, 188, 195, 970; 436/514, 541, 169, 530; 422/56, 60, 68.1, 101

[56] References Cited

U.S. PATENT DOCUMENTS

| | | | |
|---|---|---|---|
| 4,066,509 | 1/1978 | Ceska | 435/18 |
| 4,102,747 | 7/1978 | Driscoll et al. | 435/22 |
| 4,337,310 | 6/1982 | Batz et al. | 435/22 |
| 5,093,081 | 3/1992 | Sudo et al. | 422/56 |

FOREIGN PATENT DOCUMENTS

| | | |
|---|---|---|
| 0005148 | 11/1979 | European Pat. Off. . |
| 0034692 | 9/1981 | European Pat. Off. . |
| 0134291 | 3/1985 | European Pat. Off. . |
| 0347839 | 12/1989 | European Pat. Off. . |

OTHER PUBLICATIONS

Tietz, N. W. *Textbook of Clinical Chemistry*, 1986, W. B. Saunders Company, pp. 729–734.

Derwent Publications Ltd., London, GB: Class D17, AN 70–48609R & JP–B–45– 018 954 (Nagase Sangyo Co. Ltd. abstract.

Derwent Publications Ltd., London, GB; AN 8608047, & JP–A–61 031 954 (Hitachi KK) 14 Feb. 1986 abstract.

*Primary Examiner*—James C. Housel
*Assistant Examiner*—Nancy J. Parsons
*Attorney, Agent, or Firm*—McAulay Fisher Nissen Goldberg & Kiel, LLP

[57] ABSTRACT

An immunoassay element for quantitatively analyzing a ligand by determining the change in enzymatic activity. When the ligand is a low molecular weight antigen, competitive reactions between the ligand, enzyme-labelled antibody and conjugate of the antigen and high molecular weight compound are utilized. When the ligand is a macromolecular antigen, a reaction between the ligand and an enzyme-labelled antibody is utilized directly. The immunoassay element comprises a substrate layer containing a non-diffusible substrate which forms a diffusible material in the presence of the enzyme, and a reagent layer for detecting the thus formed diffusible material. The non-diffusible substrate is composed of a pulverized insoluble polysaccharide. The reagent layer may further contain a fragmenting enzyme for further fragmenting the non-diffusible material. Also provided are processes for quantitatively analyzing both of low molecular weight and macromolecular antigens contained in any samples by the use of the immunoassay elements of the invention.

11 Claims, 4 Drawing Sheets

IMMUNOASSAY ELEMENT CONTAINING A PULVERIZED WATER-INSOLUBLE POLYSACCHARIDE AND PROCESS FOR IMMUNOASSAY

This is a continuation of application Ser. No. 07/846,804, filed Mar. 4, 1992 now abandoned.

BACKGROUND OF THE INVENTION

1. Field of the Invention

The present invention relates to a dry immunoassay element in which a homogeneous enzyme immunoassay is utilized, and an immunoassaying process in which the dry immunoassay element is used.

Analyses of the constituents originated from the living body or chemicals contained in the body fluids, such as blood and urine, are useful for diagnosing the condition of diseases or judging the course of curing, and thus they occupy important parts in the field of clinical test. The so-called enzyme immunoassay has been known in the art as one method for analyzing such constituents (ligands) generally present in a small amount in the body fluids. The enzyme immunoassay may be classified into heterogeneous systems for which B/F (Bound/Free) separation must be effected, and homogeneous system for which B/F separation is not necessary. The reactions in the homogeneous system are based on the phenomenon that the enzymatic activity of the labelling enzyme is affected by some interference caused by binding of an antibody to the antigen (ligand), and the inhibition due to antigen-antibody binding is generally utilized. It is considered that the enzymatic activity is suppressed by a steric hindrance caused by binding the enzyme to the substrate or a change in three-dimensional structure of the enzyme, when the antibody which is generally a large molecule is bound to the antigen in the enzyme-labelled antigen.

When the antigen is a high polymer, suppression of enzymatic activity by the antigen-antibody binding reaction may be detected by labelling the antibody with an enzyme.

Meanwhile, in the routine clinical tests in which a number of test samples are to be handled, it is demanded that the individual samples should be analyzed by simple operations, more desirously by automated operation sequence.

2. Prior Art Statement

To comply with the demand, dry analysis elements have been proposed (see, for example, Unexamined Japanese Patent Publication Nos. 53888/1974 (corresponding to U.S. Pat. No. 3,992,158), 77356/1984 (corresponding to EP 0097952A) and 102388/1984 and U.S. Pat. No. 4,459,358.)

A dry analysis element has been known, in which an enzyme-labelled antibody is utilized and reacted in a homogeneous enzyme immunological reaction (see Unexamined Japanese Patent Publication No. 321360/1989 which corresponds to EP 0347839A). This known dry analysis element comprises the following three reagent ingredients in the same or different layers in the composite multi-layered structure:

(A) An antigen having a high molecular weight (a coupling product of a ligand or a derivative thereof with a high molecular weight compound; hereinafter referred to as "polymerized antigen");

(B) A water-insoluble high polymer substrate; and (C) A conjugate of an antibody against the ligand and an enzyme for the substrate.

The antigen supplied by spotting onto the analysis element binds to the antibody-enzyme conjugate through a competitive reaction with the reaction of the polymerized antigen. The complex of antigen-antibody-enzyme reacts with the water-insoluble high polymer substrate to form a soluble lower molecular weight product. On the other hand, the complex of polymerized antigen and enzyme-labelled antibody formed by the binding with the polymerized antigen cannot exhibit the enzymatic activity to the high polymer substrate. Accordingly, as the quantity of the antigen in the sample is increased, the product produced by the enzymatic reaction increases. This product is allowed to diffuse into a detection layer where the quantity of the product is determined by measuring the optical density of an absorption resulted by the colored chemical group, to make it possible to analyze the antigen in the sample quantitatively.

The immunoassay element disclosed in Unexamined Japanese Patent Publication No. 295466/1991 (corresponding to U.S. Ser. No. 07/684,283 and EP 0451848A2) is an improvement of the aforementioned immunoassay element. This immunoassay element has a reagent layer containing a fragmenting enzyme for further fragmenting the decomposition product by the reaction of labelling enzyme, so that the fragmented lower molecular weight product is detected for further sensitization of the element.

When the analyte or ligand is a macromolecular antigen, the immunoassay element described in the specification of Japanese patent Appln. No. 248711/1990 (corresponding to U.S. patent application Ser. No. 07/763,198) may be used. This prior art element has the following two components either in a same layer or in different layers:

(A) Water-insoluble high polymer substrate; and (B) Conjugate of an antibody to the macromolecular antigen and an enzyme for the substrate.

Likewise to the immunoassay element described in the specification of Unexamined Japanese Patent Publication No. 295466/1991 a reagent layer containing a fragmenting enzyme for further fragmenting the decomposition product by the action of labelling enzyme is provided so that the fragmented product having a lower molecular weight is detected to improve the sensitivity.

Anyway, it is desirous that the activity of the labelling enzyme to the high polymer substrate is sufficiently high. However, it is considered detrimental to use a water-insoluble high polymer substrate as the substrate for the enzyme, since such a sustrate is generally a macromolecular weight compound.

OBJECTS AND SUMMARY OF THE INVENTION

The present invention has been accomplished in view of the aforementioned circumstances, and an object thereof is to provide an immunoassay element utilizing a homogeneous enzyme immunoassay for enabling a rapid analysis of an analyte at a high sensitivity using a simple operation.

Analytes which may be analyzed by the immunoassay element of the invention include both of low molecular weight antigens and macromolecular (or high molecular weight) antigens.

A further object of this invention is to provide processes for quantitatively analyzing an analyte while using the aforementioned immunoassay element.

The object of this invention is attained by the provision of an improved immunoassay element for quantitatively analyzing a low molecular weight antigen by determining the change in enzymatic activity caused by competitive reactions between an enzyme-labelled antibody and said low molecular weight antigen and a conjugate of said low molecular weight antigen with a high molecular weight compound, wherein said element comprises a substrate layer containing a non-diffusible substrate which forms a diffusible material in the presence of said enzyme and a reagent layer for detecting said diffusible material, the improvement characterized in that said non-diffusible substrate is a pulverized water-insoluble polysaccharide.

According to a further aspect of the invention, there is provided an improved immunoassay element for quantitatively analyzing a macromolecular antigen by determining the change in enzymatic activity caused by a reaction between an enzyme-labelled antibody and said macromolecular antigen, wherein said element comprises a substrate layer containing a non-diffusible substrate which forms a diffusible material in the presence of said enzyme and a reagent layer for detecting said diffusible material, the improvement characterized in that said non-diffusible substrate is a pulverized insoluble polysaccharide.

Further provided by the present invention is an immunoassaying process for quantitatively analyzing an amount of a low molecular weight antigen in a sample by determining the change in eyzymatic activity caused by competitive reactions between an enzyme-labelled antibody and said low molecular weight antigen and a conjugate of said low molecular weight antigen with a high molecular weight compound, comprising a step of:

(a) applying said sample on a substrate layer containing a non-diffusible substrate for forming a diffusible material in the presence of said enzyme, said non-diffusible substrate being a pulverized insoluble polysaccharide;

(b) allowing to migrate said diffusible material formed in said substrate layer into a reagent layer for detecting said diffusible material; and (c) measuring the amount of said diffusible material migrating into said reagent layer.

Still further provided by the invention is an immunoassaying process for quantitatively analyzing an amount of a macromolecular antigen in a sample by determining the change in eyzymatic activity caused by a reaction between an enzyme-labelled antibody and said macromolecular antigen, comprising a step of:

(a) applying said sample on a substrate layer containing a non-diffusible substrate for forming a diffusible material in the presence of said enzyme, said non-diffusible substrate being a pulverized insoluble polysaccharide;

(b) allowing to migrate said diffusible material formed in said substrate layer into a reagent layer for detecting said diffusible material; and (c) measuring the amount of said diffusible material migrating into said reagent layer.

In a preferred embodiment, a fragmenating enzyme for further fragmenting the diffusible material may be contained in the reagent layer or a layer underlying below the reagent layer so that the fragmented product having a lower molecular weight is detected.

In a modified embodiment, the high polymer antigen and the enzyme-labelled antibody may be contained in the substrate layer or another layer laminated on the substrate layer.

When the analyte (ligand) is a low molecular weight antigen, a polymerized antigen (i.e. a conjugate or linked product of the ligand and a high molecular weight compound) may be used.

The enzymatic activity of the enzyme of the enzyme-labelled antibody, which is bound to the polymerized antigen, to a non-diffusible substrate is hindered by the steric hindrance. On the contrary, the enzyme of the enzyme-labelled antibody, which is combined with the antigen contained in the sample (i.e. the ligand), keeps its original enzymatic activity to the non-diffusible substrate. As a result, the quantity of the diffusible material formed in the substrate layer is proportional to the quantity of the antigen contained in the sample. The diffusible material formed in the substarate layer migrates rapidly into the reagent layer and may be detected in a reagent layer. The unreacted non-diffusible substrate is held in the substrate layer.

When the analyte is a macromolecular antigen having high molecular weight, such as plasma or a serum protein, the enzymatic activity of the enzyme of the enzyme-labelled antibody, which is bound to the macromolecular antigen contained in the sample, to a non-diffusible substrate is hindered by the steric hindrance. As a result, the quantity of the diffusible material formed in the substrate layer is in inverse proportion to the quantity of the antigen contained in the sample. The diffusible material formed in the substrate layer migrates rapidly into the reagent layer and may be detected in the reagent layer. The unreacted non-diffusible substrate is held in the substrate layer.

DESCRIPTION OF THE PREFERRED EMBODIMENTS

Figure 1:
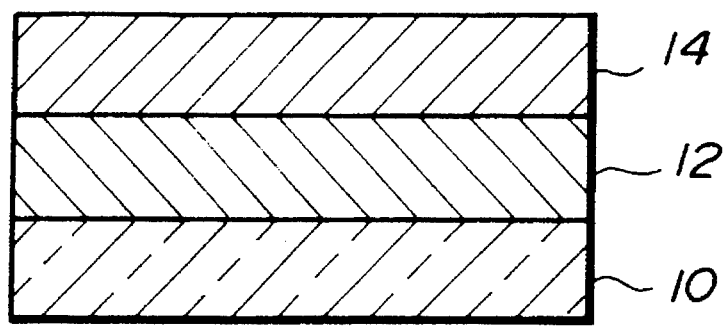
FIG. 1 is an illustration showing the principal layer structure of one embodiment of the immunoassay element according to this invention.

Layer Construction of Immunoassay Element:

FIG. 1 shows an embodiment of the immunoassay element according to this invention.

In this Figure, reference numeral 10 designates a transparent support on which laminated are reagent layer 12 and a substrate layer 14.

The substrate layer 14 is composed of a water-permeable material and contains a non-diffusible substrate for a labelling enzyme which forms a conjugate with the antibody.

The reagent layer 12 is composed of a water-permeable material and contains a reagent composition for detecting the diffusible material which has been diffused or migrated from the substrate layer. In a preferred embodiment, the reagent layer 12 further contains a fragmenting enzyme for further fragmenting the diffusible material into a lower molecular weight product, so that the reagent composition detects the thus formed lower molecular weight product.

The principal structure of the immunoassay element of the invention, as described in the preceding paragraph, is identical irrespective of whether the analyte is a low molecular weight antigen or a high molecular weight antigen. However, when the analyte is a low molecular weight antigen, the mixture is spotted on or otherwise supplied to the substrate layer 14, the mixture containing the reaction product of low molecular weight antigen in the sample with the enzyme-labelled antibody and the competition reaction product of the conjugate of the antigen and the high molecular weight compound with the enzyme-labelled antibody. In such a case, the amount of the formed diffusible material is increased as the amount or content of the ligand (low molecular weight antigen) is large or high. On the other hand, when the analyte is a high molecular weight or macromolecular antigen, the antigen-antibody binding reaction is effected only between the analyte and the enzyme-labelled antibody, and the reaction mixture is spotted on or otherwise supplied to the substrate layer 14. In the latter case, the amount of the formed diffusible material is decreased as the amount of the ligand (macromolecular antigen) is large.

Analyte (Substance to Be Analyzed)

The substance to be analyzed by the present invention (hereinafter referred simply as "analyte") is a ligand having an antigenic determinant and contained in the sample.

The sample containing the analyte is not limited and many kinds of sample may be analyzed by this invention, the typical examples including blood (whole blood, blood plasma, blood serum), lymph fluid and urine. It is preferred to preclude suspended particles, such as blood cells, when such particles are present. However, a sample may be directly spotted on the analysis element of this invention without precluding such suspended particles when the analysis element has a filter layer, according to a preferred embodiment of this invention.

Any ligands may be analyzed by the use of the analysis element of this invention, as far as each ligand acts as an antigen and an antibody therefor can be provided.

Examples of low molecular weight antigen include medicines such as digoxin, theophylline, phenobarbital, phenytoin, penicillin, amikacin, derivatives of these medicines (for example, complexes of medicines with living components, such as proteins), prostaglandin and hormones such as testosterone, progesterone and thyroxine.

Examples of macromolecular weight antigen include hormons secreted from various endocrine glands, plasma proteins such as immunoglobulin, albumin, ferritin and C-reactive proteins (hereinafter referred to as CRP), viruses such as HB antigen, bacteria, and antigens present in various organs, blood and urine such as protein and α-phetoprotein and carcinoembryonic antigen (CEA).

Meanwhile, the high polymer antigens as referred to throughout the specification include antigens each having such a high molecular weight as exerting an interfering (suppressing) action on the enzymatic activity of the labelling enzyme, for instance, having a molecular weight of not less than 20,000 daltons, more preferably not less than about 50,000 daltons. On the other hand, the low molecular weight antigens as referred to throughout the specification include antigens each having a molecular weight low enough not to affect the enzymatic activity of the enzyme-labelled antibody, for instance, having a molecular weight of less than 20,000 daltons. However, it should be noted here that the aforementioned specific numerical value is a tentative dividing line and that the judgment on the recognition of whether one ligand is a low molecular weight antigen or a high molecular weight antigen should be made in consideration of the system whether the competition reactions between the specific analyte antigen and a certain linked product of a high polymer compound (polymerized antigen) are utilized or not.

Polymerized Antigen

The polymerized antigen, i.e. the linked product of the ligand and a large molecule or high molecular weight compound, is bound to an antibody to suppress the activity of the enzyme which is conjugated with the antibody for labelling the latter. The polymerized antigen is used when the analyte is a low molecular weight antigen, and is not used when the analyte is a high molecular weight antigen.

It is preferable that the used high molecular weight compound is water-soluble and has a molecular weight of not less than 50,000 daltons. Examples of usable high molecular weight compound are proteins such as gelatin, hemocyanin and ferritin, and polyethylene glycol. It suffices that these compounds satisfy the aforementioned conditions when bound to the ligands, and those having relatively lower molecular weights, such as bovine serum albumin, can also be used by polymerizing them, for example, by auto-polymerization.

The method for linking the ligand to the high molecular weight compound may be selected in considering the functional groups of the both reactants. Utilizable functional groups include, for example, amino, carboxyl, hydroxyl, thiol, imidazole and phenyl. For example, amino groups may be linked to each other by a number of known methods, such as isocyanate method, glutaraldehyde method, difluorobenzene method and benzoquinone methods. An amino groups may be linked to a carboxyl group by a method in which the carboxyl group is converted to succinylimide ester, or by other methods including the carbodiimide method, Woodward reagent method and the periodic acid oxidation method (Nakane method) in which the amino group is linked with a sugar chain. When a thiol group is utilized, one of the carboxyl groups is converted to succinylimide ester which is reacted with cysteine to introduce a thiol group and then both groups are linked to each other using a bifunctional linking reagent which reacts with the thiol group. The methods in which the phenyl group is utilized include the diazotization method and the alkylation method. The linking method is not limited to the aforementioned methods, and may be selected from the methods described in "Method in Immunology and Immunochemistry", vol. 1, (C. A. Williams, M. W. Chase, Academic Presss (1967)) or "KOSO MEN'EKI SOKUTEI-HO" (Enzyme Immunoassay), edited by Ishikawa, Kawai and Miyai, Igaku Shoin, 1978. The ligand may be linked to the high polymer compound at any desired ratio. After the completion of the linking reaction, the reaction product is refined by the gel filtration or the ion exchange chromatography, and may be dried by the lyophilizing process as desired.

The ligand per se may be polymerized to obtain a polymerized antigen. Polymerization of the ligand may be effected similar to the aforementioned linking methods. For example, the ligand may be polymerized by using a bifunctional cross-linking agent such as carbodiimide or glutaraldehyde.

In lieu of the ligand, the high molecular weight compound may be linked to a derivative of the ligand having immunological cross-reactivity to a corresponding antibody for the ligand. Meanwhile, the derivatives of the ligand include not only those which have analogous chemical structures but also those which exhibit analogous behaviors in their immunological reactivities. For instance, when an antibody against theophylline as the ligand cross-reacts immunologically with caffeine, derivatives of caffeine may also be used as materials for forming the polymerized antigen.

When the ligand or a derivative thereof has not a proper functional group to be linked to a high molecular weight compound, an amino group, a carboxyl group or a thiol group may be introduced into the ligand or the derivative thereof. Such a group may be introduced through a spacer to facilitate linking thereof to a high molecular weight compound. For example, when the ligand is theophylline, a carboxyl group may be introduced to obtain 8-propylcarboxyltheophylline which is linked to a high molecular weight compound.

Antibody

The antibody labelled with an enzyme is a specific antibody against the ligand which is an analyte. When a derivative of the ligand is used for forming the large molecule antigen, an antibody which reacts with the antigenic determinant common to the ligand and the derivative thereof. The antibody may be obtained by the conventional process, a monoclonal antibody may be preferably used to improve the sensitivity. The antibody may be a protein fragment, such as F (ab')$_2$, Fab'or Fab.

Labelling Enzyme, Non-Diffusible Substrate and Fragmenting Enzyme

The enzyme bound to the antibody as the label decomposes the non-diffusible high polymer substrate to produce a diffusible product, which may be fragmented or decomposed to a yet lower molecular weight product by the action of the fragmenting enzyme.

The non-diffusible substrate is not dispersible into an aqueous sample liquid and neither diffused nor migrated into the reagent layer 12 by itself.

The fragmenting enzyme is contained in the reaction layer 12 and converts the diffusible product produced from the non-diffusible substrate by the action of the labelling enzyme bound to the antibody to form a lower molecular product which can be detected.

A suitable combination of enzyme and substrate may be selected so that an enzyme acts on the non-diffusible substrate to form a diffusible substance which is further decomposed by the fragmenting enzyme to produce a lower molecular weight product which is easily detected, Labelling Enzyme Examples of suitable enzyme (labelling enzyme) include hydrolases which form diffusible oligomers from non-diffusible substrates composed of polymers, a specific example being glucosidase. Examples of glucosidase are α-amylase, β-amylase, glucoamylase and lysozyme.

The enzyme and the antibody may be conjugated similar to the linking between the high molecular weight compound and the antigen.

It is preferred that the enzyme is not affected by any hindering factor present in the sample, and that a competitive enzyme of same kind is not present in the sample. However, when an enzyme which is same as the labelling enzyme is present in the sample, an enzyme inhibitor may be used. The enzyme inhibitor may be one which inhibits the enzyme in the sample to a greater extent than the inhibiting activity towards the labelling enzyme. It is most preferable that the enzyme inhibitor entirely inactivates the enzyme in the sample and does not deactivate the labelling enzyme. However, in practical use, it suffices that the blank value is not raised at the determination step and the enzyme inhibitor may be inactivated to restore the activity of the enzyme in the sample after the completion of determination. It also suffices if the enzyme inhibitor does not inhibit the enzyme in the enzyme-labelled antibody, but can inhibit the activity of free enzyme. The enzyme inhibitor may be selected from known enzyme inhibitors so that the selected enzyme has the specific characteristics as aforementioned. Otherwise, an antibody against the enzyme which contained in a sample to cause a problem is prepared and used as an enzyme inhibitor.

Non-Diffusible Substrate

According to an important feature of this invention, a pulverized water-insoluble polysaccharide is used as the non-diffusible substrate.

Examples of the substrate for said α-amylase, β-amylase or glucoamylase are carboxymethylated starch and starch.

When carboxymethylated starch or starch is used as the non-diffusible substrate, it may be combined with such a labelling enzyme as α-amylase and may also combined with such a fragmenting enzyme as glucoamylase or α-glucosidase which will be described in detail hereinafter.

Particularly convenient insoluble polysaccharides which may be used in this invention is starch. Starch is well known in the art, and may be produced from various resources such as potato, corn, wheat and sweet potato. Commercial products of water-insoluble carboxymethylated starch include, for example, EXPROTAB (Produced by Edward Mendel company Inc.) and BONTAB 30 (produced by Nichiden Chemical Co., Ltd.).

Insoluble polysaccharides may be pulverized into fine particles, for example, by cutting by blades, crushing in the freezed state or using a fluid energy mill (e.g. jet mill), the particularly preferred method being milling by a jet mill. Amongst the milling with jet mills, it is preferable to use a single track jet mill. After being pulverized into fine particles, they are classified by means of wet centrifugal classification or dry centirifugal classification, the dry centrifugal classification being preferred. The most preferred dry classification method is to use the spedic classifier.

According to an important feature of the invention, the activity of the insoluble polysaccharide to the labelling enzyme is enhanced by pulverization of the particles of the used polysaccharide. The detailed reason for the enhancement of the activity to the enzyme has not been clarified. However, it would be estimated that the steric hindrance by the substrate, which is a macro-molecule in itself and thus hinders the uncoupling reaction of the chemical bond at which the substrate is hydrolyzed by the action of the approaching enzyme, is alleviated as the particle size of the substrate is decreased. In view of the above, it is considered that the better result can be obtained as the particle size of the insoluble polysaccharide becomes smaller. However, as the particle size of the substrate becomes too small, the labelling enzyme approaches to the hydrolyzed site of the substrate too easier to decompose the substrate, leading to an inconvenient result that the labelling enzyme conjugated with the antibody which has been bound to the polymerized antigen (or macromolecular antigen) exhibits high activity. As a result, the S/N ratio of the analysis element is lowered to an extent not to suit for practical use. Accordingly, the particle size of the insoluble polysaccharide should be determined in consideration of the balance between the enhancement of the enzymatic activity and the decrease in S/N ratio. It has been found that the preferable average particle size or diameter of the insoluble polysaccharide ranges from 3 to 32 μm. More preferably, the average particle size ranges from 3 to 10 μm, particularly from 3 to 5 μm.

The pulverized insoluble polysaccharide may become a more preferable substrate by denaturating the same by using an alkali or by heating. Although the reason for the enhancement of enzymatic activity by such a denaturation can not clearly elucidated, it is presumable that the surface condition of the insoluble polysaccharide, which is a macro molecule, is somehow changed to allow easy access or approach of the activity center of the enzyme to the hydrolyzed site of the polysaccharide to accelerate the decomposition thereof.

The alkali-denaturation is a denaturation process in which an organic base such as triethylamine, diisopropylamine, n-butylamine, etc. or an inorganic base such as $NaHCO_3$, KOH, NaOH, etc is used. In this process, pH value of the treating solution should be maintained within pH 9 to pH 14, most preferably within pH 11 to pH 13, and the treating time ranges generally from 0.5 to 36 hours, preferably from 1 to 3 hours. The temperature is preferably maintained within the range of from 0° C. to 40° C. during this treatment. The reaction mixture must be neutralized after denaturation with an alkali. Neutralization may be effected by the conventional method while using hydrochloric acid, acetic acid or sulfuric acid, and it is most preferred that neutralization is effected by the use of acetic acid which would uncouple the glucoside bonds of starch at the least.

When soluble components (high polymer polysaccharides) are formed during the pulverization or denaturation step, it becomes necessary to separate the thus formed soluble components from the insoluble polysaccharide. Separation of the soluble components may be effected by any of the known processes, for example, by centrifugal separation. When Exprotab is used as the carboxymethylated starch, the degree of the particular centrifugal separation may be confirmed by measuring the electric conductivity of the supernatant layer of the centrifuged mixture since the soluble products formed by decomposition of EXPROTAB has some electric charge. The degree of separation or purification may be confirmed by detecting the formed soluble components by means of any known coloring reactions of these saccharides. The most convenient method of producing powders of the insoluble polysaccharides dispersed in the dispersion is the method wherein the insoluble polysaccharides are precipitated by the use of any known organic solvent followed by filtration and drying of the precipitate.

Fragmenting Enzyme

The fragmenting enzyme may be an enzyme of the same kind as of the labelling enzyme. In such a case, it is preferred that the labelling enzyme is an endo-active enzyme which fragments the molecule intramolecularly to produce an oligomer, and that the fragmenting enzyme is exo-active and acts at the terminal of the molecule to produce a monomer. For instance, when the non-diffusible substrate is a polymer (e.g. starch), a fragmenting enzyme for decomposing the diffusible oligomer (e.g. maltose) produced by the action of the labelling enzyme to a monomer (e.g. glucose) is used. Examples of the fragmenting enzyme include hydrolases for saccharides, specific examples being α-amylase, β-amylase, glucoamylase and α-glucosidase.

When carboxymethyl cellulose is used as the non-diffusible substrate and cellulase is used as the labelling enzyme, C1 enzyme may be used as the fragmenting enzyme.

The lower molecular weight product produced by fragmentation in the reagent layer by the action of the fragmenting enzyme may be optically detected by using a known detection reagent.

Any known methods may be employed for detecting the glucose by the action of the aforementioned fragmenting enzyme. Examples include a method in which hydrogen peroxide formed by the oxidation of glucose in the presence of glucose oxidase is detected (e.g. the method wherein a Trinder reagent is used, as described in Ann. Clin. Biochem., 6, 24 (1964) and J. Clin. Pathol., 22, 246 (1969), the method wherein a Trinder reagent is used, as described in Unexamined Japanese Patent Publication No. 50991/1974 (corresponding to U.S. Pat. No. 3,886,045), U.S. Pat. No. 3,992, 158 and Unexamined Japanese Patent Publication No. 164356/1980 (corresponding to U.S. Pat. No. 4,292,272), the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts, 99, (1983): 209284j), the method wherein a reagent containing an imidazole leuco dye substituted with a diarylmonoaralkyl, as described in Unexamined Japanese Patent Publication Nos. 193352/1984 (corresponding to EP 0122641A) and 224677/1985 (corresponding to U.S. Pat. No. 4,665,023)), a method wherein NADH produced in the presence of glucose dehydrogenase and NAD is detected, and a method wherein glucose-6-phosphate produced in the presence of hexokinase is detected. Among these detection methods, the most preferred is the method wherein glucose is oxidized in the presence of glucose oxidase to form hydrogen peroxide which is detected using peroxidase and a leuco dye because of its high detection sensitivity.

These detection reagents may be contained in the reagent layer 12 together with the fragmenting enzyme, or may be contained in another layer disposed below the reagent layer 12 (for example in a second reagent layer or a detection layer) to detect the lower molecular weight product produced. When a leuco dye is used, it is preferred that the dye is dispersed in the hydrophilic binder in the solution in a water-immiscible solvent in consideration of the stability of the formed dye.

Layer Structure of the Analysis Element

The dry immunoassay element of this invention may have a layer structure similar to those of various dry analysis elements. The element may be of a multi-layered construction including, in addition to the substrate layer and the reagent layer, a support, a spreading layer, a detection layer, a light-shielding layer, an adhesive layer, a water-absorbing layer, an undercoating layer and so on. Examples of such analysis elements are disclosed in the specifications of Unexamined Japanese Patent Publcication Nos. 53888/1974 (corresponding to U.S. Pat. No. 3,992,158), 40191/1976 (corresponding to U.S. Pat. No. 4,042,353), 164356/1980 (corresponding to U.S. Pat. No. 4,292,272) and 4959/1986 (corresponding to European Patent Publication No. 0166365A).

When a light-transmitting and water-impermeable support is used, the dry immunoassay element having the following construction may be used, although the present invention is not limited to the following constructions.

(1) A reagent layer disposed on a support, and a substrate layer superposed on the reagent layer;

(2) A reagent layer disposed on a support, an adhesive layer superposed on the reagent layer and a substrate layer superposed on the adhesive layer in this order;

(3) A support, and a detection layer, a reagent layer and a substrate layer superposed in this order;

(4) A support, and a reagent layer, a light-shielding layer, and a substrate layer superposed in this order;

(5) A support, and a detection layer, a reagent layer, light-shielding layer and a substrate layer superposed in this order;

(6) A support, and a detection layer, a light-reflecting layer, a reagent layer and a substrate layer superposed in this order;

(7) A support, and a second reagent layer, a light-reflecting layer, a first reagent layer and a substrate layer superposed in this order; and (8) A support, and a detection layer, a second reagent layer, a light-reflecting layer, a first reagent layer and a substrate layer superposed in this order.

In the constructions (1) to (6), the reagent layer may be composed of plural layers. The reagent layer may be an immunological reaction layer which contains a component capable of taking part in a immunological reaction, as will be described hereinafter.

A water-absorbing layer may be disposed between the support and the reagent or detection layer. Filtering layers may be interposed between the adjacent layers. A spreading layer may be disposd on the substrate layer, or the substrate layer may serve also as a spreading layer.

Substrate Layer

The substrate layer 14 is composed of a water-permeable layer and contains a non-diffusible substrate which is a substrate for the enzyme labelling the antibody.

In order to ensure water-permeability of the substrate layer, it is preferable that the substrate layer is composed of a porous medium or a layer composed of a hydrophilic polymer binder.

The porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material include a membrane filter composed of cellulose acetate described in Unexamined Japanese Patent Publication No. 53888/1974 (corresponding to U.S. Pat. No. 3,992,258), and a particulate structure layer containing interconnected voids and composed of inorganic or organic fine particles as disclosed in Unexamined Japanese Patent Publication Nos. 53888/1974 (corresponding to U.S. Pat. No. 3,992,258), 90859/1980 (corresponding to U.S. Pat. No. 4,258,001) and 70163/1983 (correponding to U.S. Pat. No. 4,486,537). A laminated structure made of partially bonded multiple porous layers may also be preferably used, examples of such structure being disclosed in Unexamined Japanese Patent Publication Nos. 4549/1986 (corresponding to EP 0166365A), 116258/1987 (Chemical Abstracts, 108, (1988): 3041y), 138756/1987 (EP 0226465A), 138757/1987 (EP 0226465A) and 138758/1987 (EP 0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent publication No. 66359/1982 (corresponding to GB 2,087,974A and U.S. Pat. No. 4,783,315). In order to adjust the area or rate for spreading, the spreading layer may contain a hydrophilic polymer or a surfactant as described in Unexamined Japanese Patent publication Nos. 222770/1985 (corresponding to EP 0162301A), 219397/1988 (corresponding to DE 37 17 913A), 112999/1988 (corresponding to DE 37 17 913A), and 182652/1987 (corresponding to DE 37 17 913A).

One convenient method is a method wherein the substrate is impregnated into or coated on a porous membrane made of, for example, paper, cloth or a high polymer, and then the composite is applied on another water-permeable layer, for example, a reagent layer superposed on the support by a method as described in Unexamined Japanese Patent publication No. 164356/1980 (corresponding to U.S. Pat. No. 4,292,272). A further method comprises the steps of bonding a porous layer on another water-permeable layer (for example a reagent layer) by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer made by any of the aforementioned methods is not limited, the thickness may range within 1 µm to 50 µm, and preferably, from 2 µm to 30 µm, when the layer is provided as a coating layer. When it is provided by another method, for example by piling of a laminate, the thickness thereof may be varied within a wide range of from several tens of µm to several hundreds of µm.

The substrate layer may be a water-permeable layer composed of a hydrophilic polymer binder, such as, gelatin and derivatives thereof (e.g. phthalated gelatin), derivatives of cellulose (e.g. hydroxyethyl cellulose), agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

The substratre layer composed of a hydrophilic polymer binder may be provided by coating an aqueous solution or dispersion of the substrate, an additional other reagent composition and a hydrophilic polymer binder on another layer, such as a support or a detection layer, and then drying the coated solution or dispersion, as disclosed in the specifications of Japanese Patent Publication No. 21677/1988 (corresponding to U.S. Pat. No. 3,992,158), Unexamined Japanese Patent publication Nos. 164356/1980 (corresponding to U.S. Pat. No. 4,292,272), 101398/1979 (corresponding to U.S. Pat. No. 4,132,528), and 292063/1986 (Chemical Abstracts, 106, (1987): 210567y). The thickness of the dried substrate layer containing a hydrophilic polymer as the binder may range from about 2 µm to about 50 µm, and preferably, from about 4 µm to about 30 µm, and the coverage thereof may range from about 2 $g/m^2$ to about 50 $g/m^2$ and preferably from about 4 $g/m^2$ to about 30 $g/m^2$.

To improve the characteristics, such as, coating characteristics, diffusibility of the diffusible material, reactivity and storage stability, the substrate layer may include, in addition to the non-diffusible substrate, various organic or inorganic additives, for example, enzyme activators, coenzymes, surfactants, pH buffer reagents, fine particles, antioxidants, etc. Examples of buffer system, which may be contained in the substrate layer, include pH buffer reagents as described in "KAGAKU BINRAN, KISOHEN" edited by Japanese Chemical Society (MARUZEN, Tokyo, 1966), pp1312–1320; R. M. C. Dawson et al., "Data for Biological Research", 2nd Edition (Oxford at the Clarendon Press, 1969), pp476–508; "Biochemistry", 5, pp467–477 (1966); and "Analytical Biochemistry", 104, pp300–310 (1980). Specific examples of usable buffers are buffer reagents containing tris(hydroxymethyl)aminomethane (Tris), buffer reagents containing phosphates, buffer solutions containing borates, buffer reagents containing citric acid or citrates, buffer reagents containing glycine, buffer solutions containing Bicine, and buffer reagents containing HEPES.

Reagent Layer

The reagent layer 12 contains a reagent composition for detecting the diffusible material which has diffused and migrated from the substrate layer 14. As desired, a fragmenting enzyme may be contained in the detection reagent composition and a detection reagent composition for detecting the lower molecular weight product formed by the action of the fragmenting enzyme may also be contained.

The reagent layer is composed of a water-permeable layer which is preferably a continuous layer made of a hydrophilic polymer binder, similar to the water-permeable layers as described in the description of the substrate layer. The used hydrophilic polymer binder may be determined in consideration of the diffusible product formed in the substrate layer and the coloring reagent contained in the reagent layer.

Support

The support 10 may be light-nontransmitting (opaque), light-semi-transmitting (translucent) or light-transmitting (transparent), and it is generally preferable that the support is light-trasmitting and water-impermeable.

Preferable materials for the light-transmitting and water-impermeable support are polyethylene terephthalate and polystyrene. In general, an undercoating is provided or the support is subjected to hydrophilization treatment in order to firmly adhere the hydrophilic layer.

Immunological Reaction Layer

The substrate layer 14 shown in FIG. 1 may contain enzyme-labelled antibody, in addition to the diffusible substrate, to form an immunological reaction layer in which an immunological reaction takes place. With such a construction, a homogeneous enzyme immunological reaction takes place in the element only by spotting a sample on the element.

Alternatively, the enzyme-labelled antibody may be contained in a separate layer other than the substrate layer.

Figure 2:
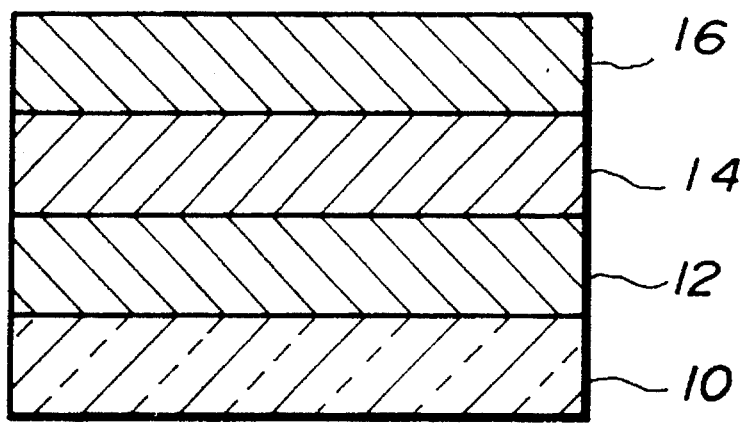
FIG. 2 is an illustration showing another embodiment of the immunoassay element according to this invention.

For example, as shown in FIG. 2, the immunoassay element may comprise a water-permeable layer 16 containing the enzyme-labelled antibody and superposed on the substrate layer 14. With such a construction, the low molecular weight or high molecular weight antigen in the sample binds with the antibody of the enzyme-labelled antibody contained in the layer 16, and then migrates into the substrate layer 14.

When the analyte is a low molecular weight antigen, the polymerized antigen (the conjugate of the antigen and a high molecular weight compound) may also be contained in the substrate layer 14 or the separate layer 16.

In order to contain an enzyme-labelled antibody in a separate layer in the substantially dry state or in the substantial absence of water, the enzyme-labelled antibody may be dissolved or dispersed in a non-aqueous medium, such as an alcohol (e.g. ethanol) and then the solution or dispersion is impregnated in the water-permeable layer.

Process for Preparing the Immunoassay Element

The dry immunoassay element of the invention may be prepared by any of the known processes described in the specifications of aforequoted patents.

The analysis element of the invention may be cut into a square piece having sides each ranging from about 15 mm to about 30 mm or a disk having a substantially the same area. It is preferred, in view of the preparation, packaging, shipping, storage and measuring operations, that the element be contained in a slide frame as disclosed, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For the convenience in some uses, it may be formed in a tape shape which is contained in a cassette or magazine, or a small piece thereof may be applied on or contained in a card having an opening.

Analyzing Method Using the Immunoassay Element

The analysis element of the invention may be used for the quantitative analysis of an analyte ligand in a sample liquid by using it through the operations described in the specification of the aforequoted patents.

For example, about 5 µl to about 30 µl, preferably 8 µl to 15 µl, of an aqueous sample liquid, such as, serum, plasma or urine, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the ligand contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/1985, 294367/1986 and 161867/1983 (the last-mentioned Publication corresponding to U.S. Pat. No. 4,424,191) to realize a quantitative analysis at a high accuracy by extremely easy operations.

Meantime, a semi-quantitative analysis may be conducted by judging the degree of coloring by naked eye if such visual judgment is adequate for the object or required accuracy.

When the analysis element does not contain the polymerized antigen and the enzyme-labelled antibody, the aqueous sample liquid is mixed with a solution containing the polymerized antigen and the enzyme-labelled antibody to complete the binding reaction, and then spotted on the substrate layer.

SYNTHESIS EXAMPLE 1

(1) Synthesis of Enzyme-Labelled Antibody (1-A) Preparation of CHM Amylase:

5 mg of Bacillus subtilis amylase was dissolved in 1 ml of a 0.1M glycerophosphate (pH 6.3), and 100 µl of a 2 mg/ml solution of [4-(maleimidomethyl)cyclohexane-1-carboxylic acid] succinimide ester (CHMS) in DMF was added thereto and allowed to react at room temperature for an hour. The reaction mixture was introduced into a Sephadex G-25 column and a 0.1M glycerophosphate (pH 6.3) was passed through the column to provide an eluted fraction containing 4-(maleimidomethyl)cyclohexane-1-carboxyamido amylase (CHM amylase).

(1-B) Preparation of Anti-Theophylline Mouse IgG F(ab')$_2$:

300 µg of papain was added to 10 mg of anti-theophylline mouse IgG (in 2 ml of 0.1M acetate buffer (pH 5.5)), and stirred at 37° C. for 18 hours. A 0.1N NaOH solution was added to the reaction liquid to adjust the pH value thereof to pH 6.0. The liquid was then introduced into a AcA-44 gel column preliminarily equilibrated with a 0.1M phosphate buffer (pH 6.3) containing 1 mM EDTA, followed by elution with the aforementioned phosphate buffer solution. The peak portion of the eluate having molecular weights of approximetely 100,000 was collected and concentrated to 1 ml to obtain the objective anti-theophylline mouse IgG F(ab')$_2$.

(1-C) Preparation of Bound of α-Amylase-Anti-Theophylline Mouse IgG Fab':

100 μl of a 10 mg/ml aqueous solution of 2-mercaptoethylamine HCl salt was added to 1 ml of a 0.1M phosphate buffer (containing 1 mM EDTA, pH 6.0) containing 6 mg of the anti-theophylline mouse IgGF(ab')$_2$ prepared in the step (1-B), and stirred at 37° C. for 90 minutes. The reaction mixture was subjected to gel filtration by a Sephadex G-25 column which was preliminarily equilibrated with a 0.1M phosphate buffer (pH 6.3) to remove unreacted 2-mercaptoethylamine to obtain HS-Fab'. 2 mg of the CHM α-amylase prepared by the step (1-A) were added to HS-Fab' to react at 37° C. for 90 minutes. The reaction mixture was then subjected to gel filtration using the AcA-34 column equilibrated with a 0.1M phosphate buffered 5 mM calcium chloride solution (pH 7.0) to collect a fraction having molecular weights of not less than 200,000, and the fraction was concentrated to obtain the objective conjugate of α-amylase and anti-theophylline mouse IgGFab'. (1-D) Preparation of Anti-CRP Mouse IgG F(ab')$_2$:

300 μg of papain was added to 10 mg of anti-CRP mouse IgG (in 2 ml of 0.1M acetate buffer (pH 5.5)), and stirred at 37° C. for 18 hours. A 0.1N NaOH solution was added to the reaction liquid to adjust the pH value thereof to pH 6.0. The liquid was then introduced into an AcA-44 gel column preliminarily equilibrated with a 0.1M phosphate buffer (pH 6.3) containing lmM EDTA, followed by elution with the aforementioned phosphate buffer solution. The peak portion of the eluate having molecular weights of approximately 100,000 daltons was collected and concentrated to 1 ml to obtain the objective anti-CRP mouse IgG F(ab')$_2$. (1-E) Preparation of Bound of (α-Amylase-Anti-CRp Mouse IgG Fab':

100 μl of a 10 mg/ml aqueous solution of 2-mercaptoethylamine HCl salt was added to 1 ml of a 0.1M phosphate buffer (containing 1 mM EDTA, pH 6.0) containing 6 mg of the anti-CRP mouse IgG F(ab')$_2$ prepared in the step (1-D), and stirred at 37° C. for 90 minutes. The reaction mixture was subjected to gel filtration by a Sephadex G-25 column which was preliminarily equilibrated with a 0.1M phosphate buffer (pH 6.3) to remove unreacted 2-mercaptoethylamine to obtain HS-Fab'. 2 mg of the CHM α-amylase prepared by the step (1-A) was added to HS-Fab' to react at 37° C. for 90 minutes. The reaction mixture was then subjected to gel filtration using the AcA-34 column equilibrated with a 0.1M phosphate buffered 5 mM calcium chloride solution (pH 7.0) to collect a fraction having molecular weights of not less than 200,000, and the fraction was concentrated to obtain the objective conjugate of α-amylase and anti-CRP mouse IgG Fab'.

SYNTHESIS EXAMPLE 2

Synthesis of Polymerized Antigen (Theophyline Bovine Serum Albumin Conjugate)

5 mg of 8-propylcarboxytheophylline was dissolved in 1 ml of DMF, and added with 3 mg of N-hydroxysuccinimide and 5 mg of water-soluble carbodiimide, followed by stirring at room temperature for 2 hours, to obtain activated theophylline. 10 mg of bovine serum albumin (BSA) was dissolved in 1 ml of a 0.1M aqueous solution of sodium hydrogencarbonate and added with 500 μl of the aforementioned activated theophylline solution. The mixed solution was allowed to stand at room teperature for an hour, and then unreacted substances were removed through a Sephadex-G25 column preliminarily equilibrated with PBS to obtain 9 mg of the objective large molecule antigen (theophylline-BSA conjugate)

EXAMPLE 1

Preparation of Pulverized Carboxymethylated Starch:

Fifty kilograms of Exprotab (produced by Edward mendel Company Inc.) were pulverized by a single track jet mill (Model FS-4) to obtain 48.2 kg (Yield: 96.3%) of pulverized product having an average particle diameter of 7.8 μm. 25.81 kg of the pulverized product were classified using a spedic classifier to obtain 10.5 kg (Yield: 40.68%) of a pulverized and classified fraction having an average particle diameter of 5.0 μm. Meanwhile, the average particle diameter of the Exprotab before pulverization was 41.9 μm.

EXAMPLE 2

Alkali-Denaturation of Pulverized Carboxymethylated Starch:

Ten grams of fine Exprotab particles having an average particle diameter of 5.0 μm, which were prepared by Example 1, were dispersed in 200 ml of distilled water, added with 50 ml of a 0.5N NaOH solution, and then stirred at room temperature for an hour. The reaction mixture was neutralized with 1N acetic acid to have a pH value of 7.05, and then distilled water was added thereto until the total volume reached 1.5 liters. The mixture was subjected to high speed centrifugation at about 10,000G, the refinement by centrifugation being repeated until the electric conductivity of the supernatant reached not more than 20 μs/cm, to remove soluble components. Then, 10 liters of ethanol were added to the dispersion while stirring the latter sufficiently, and a precipitating white substance was collected by filtration under suction pressure. Thus collected white substance was dried at 30° C. for 10 hours to obtain 6.6 g (Yield: 65%) of a pulverized and alkali-denatured product of Exprotab.

EXAMPLE 3

Thermal Denaturation of Pulverized Carboxymethylated Starch:

Ten grams of pulverized Exprotab particles having an average particle diameter of 5.0 μm, which were prepared by Example 1, were dispersed in 250 ml of distilled water, and subjected to heating or thermal treatment effected at 120° C. for 8 hours in an autoclave. Similar to Example 2, the dispersion after thermal treatment was refined through repeated centrifugation, and the precipitate formed by the addition of ethanol was collected to obtain a pulverized and thermally denatured product of Exprotab (Yield: 6.0 g, 60%).

EXAMPLE 4

Figure 3:
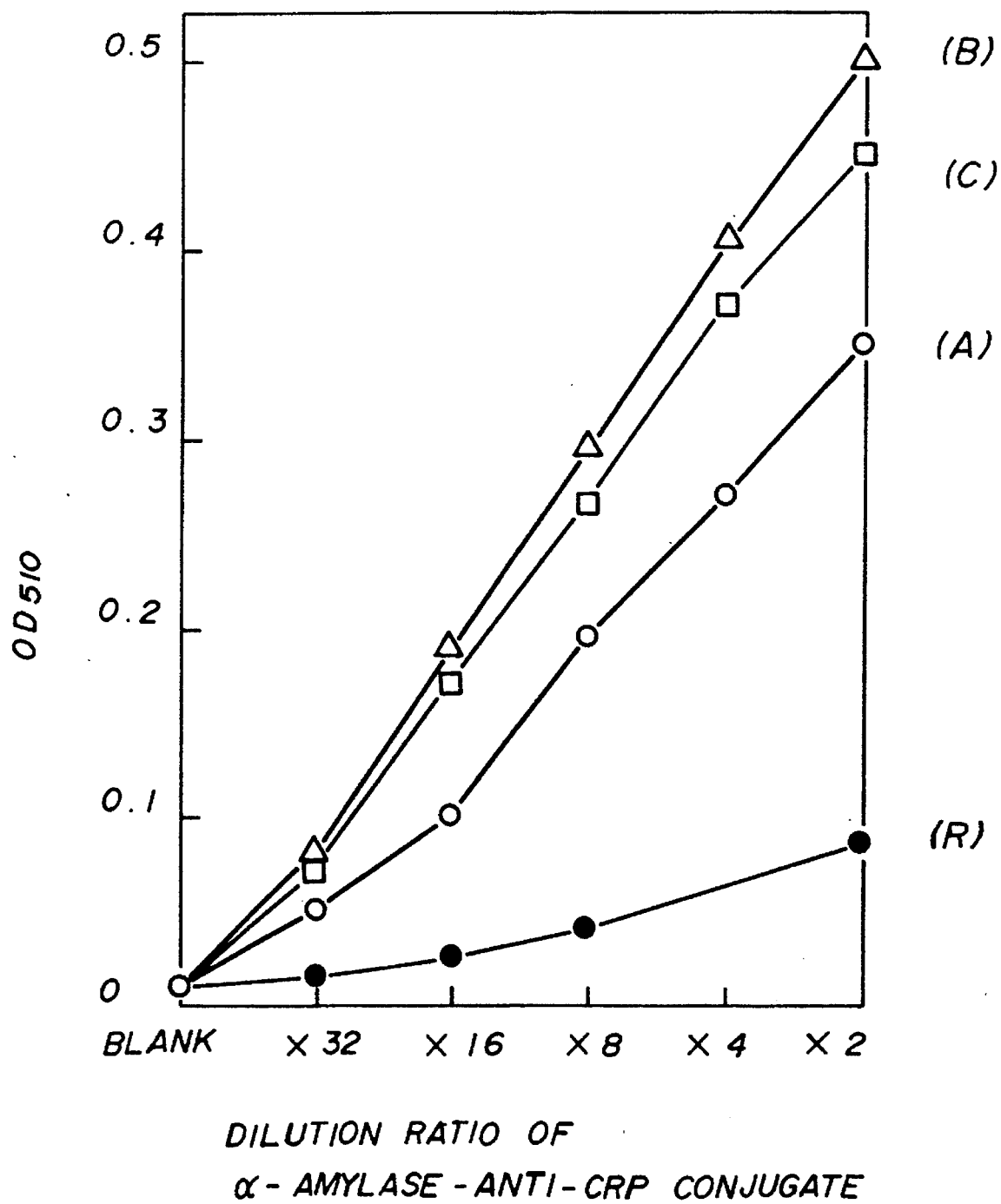
FIG. 3 is a graphic representation showing the Example 4, wherein (A) shows the activity of the finely pulverized Exprotab particles of Example 1, (B) shows the activity of the finely pulverized Exprotab particles denaturated by an alkali as described in Example 2, (C) shows the activity of the finely pulverized Exprotab particles denaturated by heating as described in Example 3, and (R) shows the activity of Comparative Example (i.e. Exprotab which has not been subjected to pulverization), respectively to the antibody labelling enzyme.

The pulverized Exprotab particles of Example 1, the alkali-denatured Exprotab particles of Example 2, the thermally-denatured Exprotab particles of Example 3 and, in addition, as a Comparative Example the commercially available Exprotab particles which have not been subjected to pulverization were dispersed, respectively, in a 50 mM maleic acid buffer solution (pH 6.5) to obtain a 0.5% (W/V) dispersion for each. 100 μl for each of diluted solutions of α-amylase-anti-CRP conjugate (which was obtained in Synthesis Example 1, (1-E)) diluted by the dilution ratios as set forth along the abscissa of FIG. 3 were added to 1 ml of each of these Exprotab dispersions, followed by incubation at 37° C. for 30 minutes. After incubation, the supernatant (500 μl) was franctionated by centrifugation, added with 100 U of glucoamylase, and then incubated at 37° C. for 2 hours. 200 μl of the supernatant was taken up and assayed on a glucose determination kit "Wako Glu C" produced by Wako Junyaku K.K. The absorbance of each assayed sample was measured at the wavelength of 510 nm. The results are shown in FIG. 3. As seen from the Figure, the pulverized product (shown by (A) in the Figure) has an enzymatic activity higher than that of the unpulverized commercial product (shown by (R) in the Figure) of Comparative Example. The alkali-denatured product (shown by (B) in the Figure) and the thermally-denatured product (shown by (C) in the Figure) have higher enzymatic activities.

EXAMPLE 5

A reagent solution containing a cross-linking reagent was coated on a colorless and transparent polyethylene terephthalate (PET) sheet (support) coated with a gelatin undercoating and having a thickness of 180 μm. The sheet was then dried, forming a reagent layer wherein the respective components had the coverages as set forth below.

| | |
|---|---|
| Alkaline-treated Gelatin | 14.5 g/m$^2$ |
| Nonylphenoxypolyethoxyethanol (Containing 9 to 10 (average) of Oxyethylene Units) | 0.2 g/m$^2$ |
| Glucose oxidase | 5,000 U/m$^2$ |
| Peroxidase | 15,000 U/m$^2$ |
| Glucoamylase | 5,000 U/m$^2$ |
| 2-(4-hydroxy-3,5-dimethoxyphenyl)-4-[4-(dimethylamino)phenyl]-5-phenethyl-imidazole (Leuco Dye) Acetate | 0.38 g/m$^2$ |
| Bis[(vinyisulfonylmethylcarbonyl)amino]-methane | 0.1 g/m$^2$ |
| An adhesive layer was coated on the reagent layer to have the following coverage, and then dried. | |
| Alkaline-treated Gelatin | 14.5 g/m$^2$ |
| Bis[(vinylsulfonylmethylcarbonyl)aminol]-methane | 0.1 g/m$^2$ |

Then, an aqueous solution containing the following reagent was coated over the surface of the adhesive layer to have the following coverages to swell the gelatin layer and a tricot knitted cloth made by knitting PET spun yarn of 36 gage corresponding to 50 deniers and having a thickness of about 250 μm was then laminated thereon, by pressing with a uniform light pressure to form a porous spreading layer.

| | |
|---|---|
| Nonylphenoxypolyethoxyethanol (Containing 9 to 10 (average) of Oxyethylene Units) | 0.15 g/m$^2$ |
| Bis[(vinyisulfonylmethylcarbonyl)amino]-methane | 0.4 g/m$^2$ |

Thereafter, a subsrate layer was formed by coating the pulverized Exprotab (having an average particle diameter of 5.0 μm) prepared by Example 1, followed by drying, to have the following coverages, to prepare a multi-layered analysis element for the quantitative analysis of theophylline.

| | |
|---|---|
| Pulverized Exprotab | 5 g/m$^2$ |
| Nonylphenoxypolyethoxyethanol (Containing 9 to 10 (average) of Oxyethylene Units) | 0.2 g/m$^2$ |

Then, a solution of the theophylline-BSA conjugate synthesized in Synthesis Example 2 was further coated to be impregnated to have a coverage of 3 mg/m$^2$ and an ethanol solution of the amylase-anti-theophylline-IgG conjugate was coated to be impregnated to have a coverage at the dry state of 3 mg/m$^2$ whereby a multilayered immunoassay element for the analysis of theophylline was prepared. The thus prepared element was cut into tips each having 1.5 cm square, and each squares was placed in a slide frame described in Unexamined Japanese Patent Publication No. 63452/1982 to prepare a multi-layered dry slide 1 for the analysis of theophylline according to this Example.

As a comparative sample, a control slide 2 having the same construction as that prepared by Example 4 except that the unpulverized Exprotab (having an average particle diameter of 41.9 μm) was used in place of the pulverized Exprotab (having an average particle diameter of 5.0 μm) for the substrate carboxymethylated starch.

10 μl for each of a 50 mM glycerophosphate buffer having a pH value of 7 and containing known quantity of theophilline was spotted on the slides 1 and 2. The slides were maintained at 37° C., and after the lapse of 4 minutes and 6 minutes, the optical density of the reflected light having a wavelength of 650 nm was measured from the support side. A calibration curve was prepared by plotting the difference in optical density ($\Delta OD_{6-4}$) of the reflected lights measured after the lapse of 4 minutes and 6 minutes.

Figure 4:
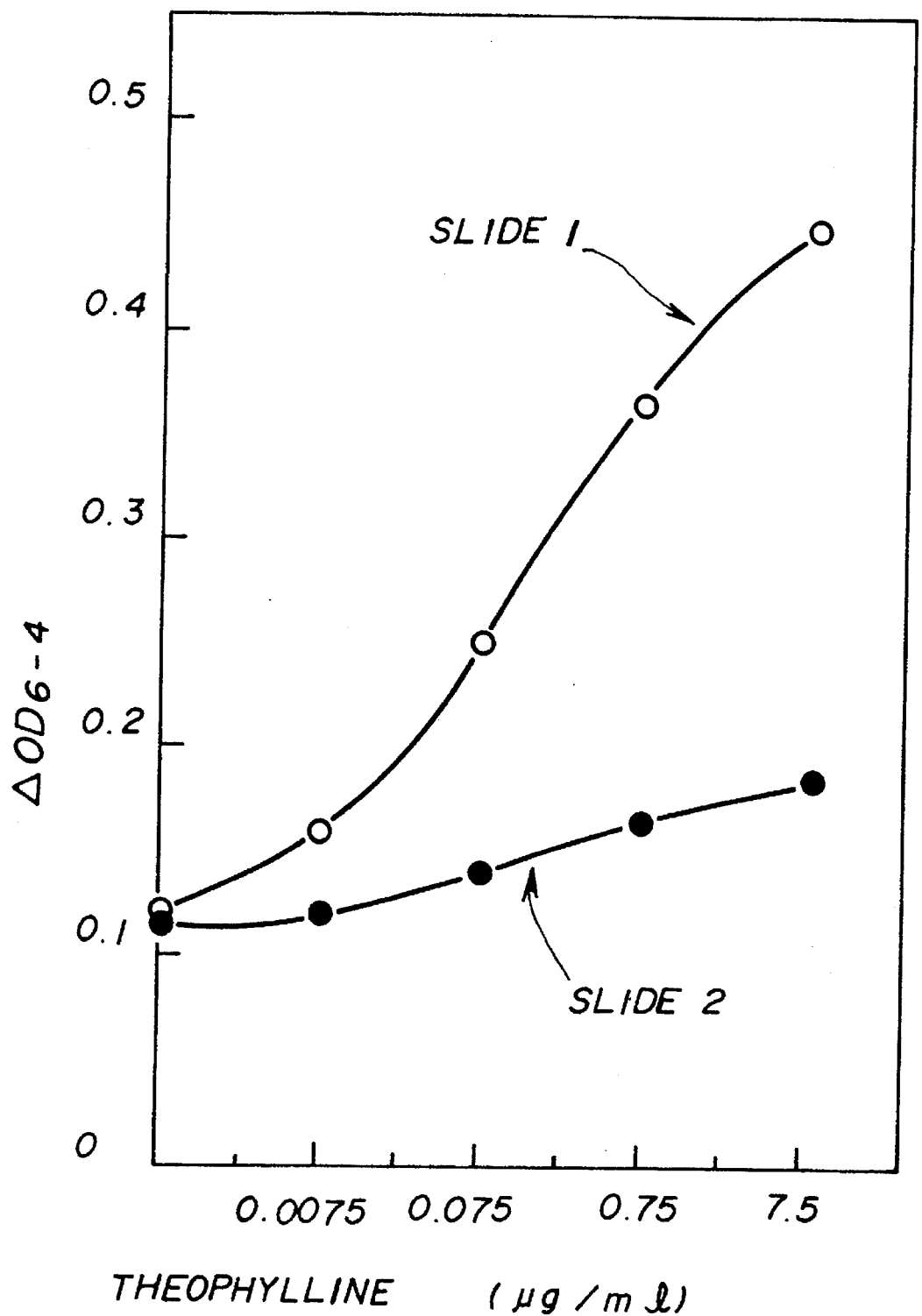
FIG. 4 is a graphic representation showing the calibration curve when the immunoassay element of Example 5 is used.

As shown in FIG. 4, the slide 1 according to the present invention exhibited a higher sensitivity when compared to the control slide 2 to give a more reliable result when used for the quantitative analysis of theophylline.

EXAMPLE 6

A reagent layer, an adhesive layer and a porous spreading layer were successively laminated on a transparent support (PET sheet) in an utterly same manner as in Example 5 to provide a construction same as described in Example 5.

A substrate layer was provided on the porous spreading layer by coating and then drying the pulverized Exprotab (having an average particle diameter of 5.0 μm) prepared by Example 1 to have the following coverage:

| | |
|---|---|
| Pulverized Exprotab | 6 g/m$^2$ |
| Nonylphenoxypolyethoxyethanol (Containing 9 to 10 (average) of Oxyethylene Units) | 0.2 g/m$^2$ |

A solution of the amylase-anti-CRP-IgG conjugate, which was prepared in Synthesis Example 1, in ethanol was coated to impregnate onto the substrate layer and then dried to have a coverage of 3 mg/m$^2$. The thus formed laminate is contained in a slide same as used in Example 5 to prepare a slide 3 of multilayered immunoassay element for the analysis of CRP.

As a comparative sample, a control slide 4 having the same construction as that prepared by Example 6 except that the unpulverized Exprotab (having an average particle diameter of 41.9 μm) was used in place of the pulverized Exprotab (having an average particle diameter of 5.0 μm) for the substrate carboxymethylated starch.

10 µl for each of a 50 mM glycerophosphate buffer having a pH value of 7 and containing known quantity of CRP was spotted on the slides 3 and 4. The slides 3 and 4 were maintained at 37° C., and after the lapse of 3 minutes and 5 minutes, the optical density of the reflected light having a wavelength of 650 nm was measured from the support side. A calibration curve was prepared by plotting the difference in optical density ($\Delta OD_{5\text{-}3}$) of the reflected lights measured after the lapse of 3 minutes and 5 minutes.

Figure 5:
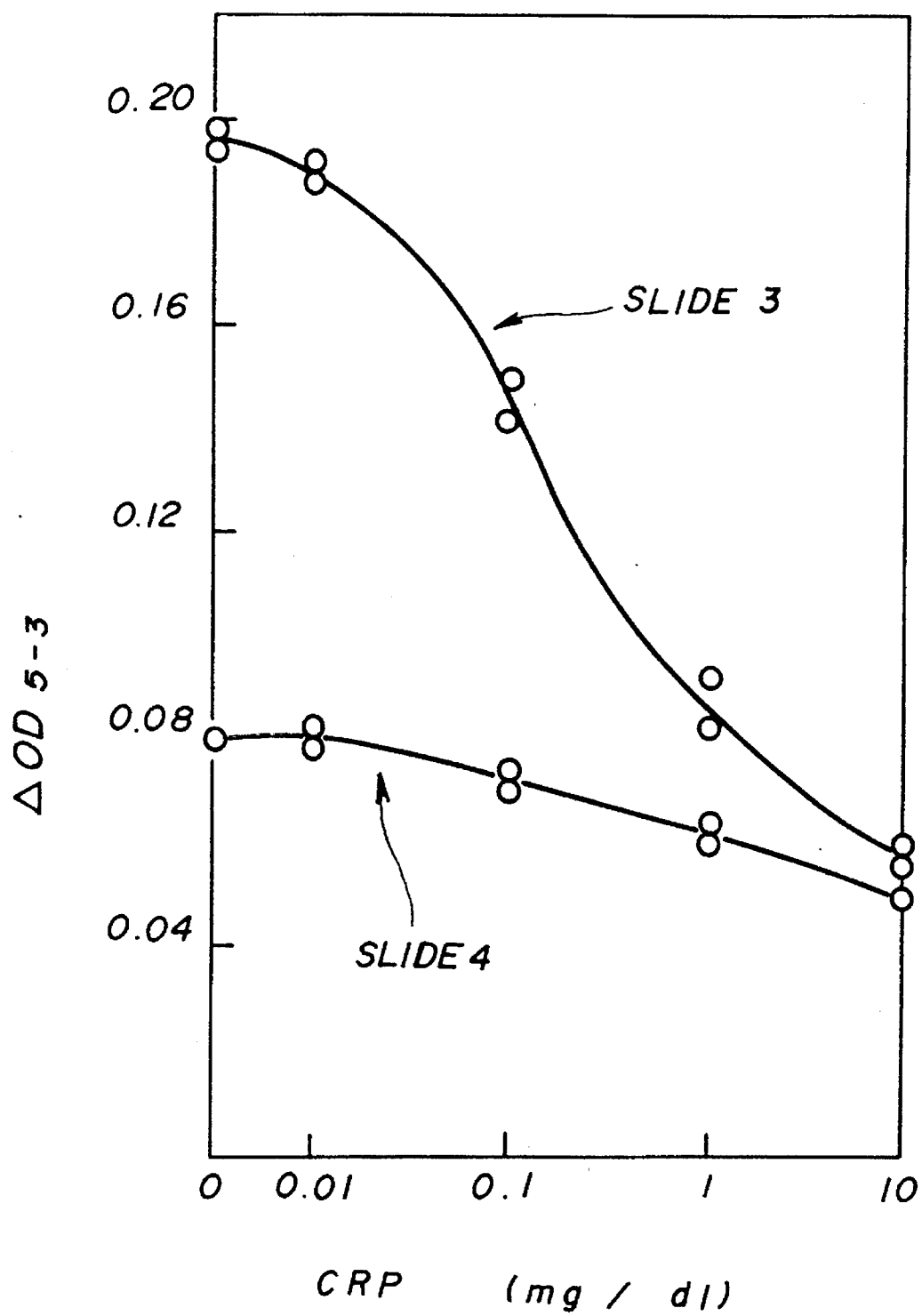
FIG. 5 is a graphic representation showing the calibration curve when the immunoassay element of Example 6 is used.

As shown in FIG. 5, the slide 3 according to the present invention exhibited a higher sensitivity when compared to the control slide 4 to give a more reliable result when used for the quantitative analysis of CRP.

EXAMPLE 7

This Example was to examine the influence of the particle size of Exprotab affecting on the enzymatic activity.

Fine particles of Exprotab having, respectively, average particle diameters of 3 µm, 5 µm, 10 µm and 32 µm were prepared through pulverization and classification carried out in the similar manner as described in Example 1. The classified Exprotab particles were subjected to alkali-denaturation in the manner as described in Example 2.

A reagent layer, an adhesive layer and a porous spreading layer were successively laminated on a transparent support (PET sheet) in an utterly same manner as in Example 5 to provide a construction same as described in Example 5. A substrate layer was provided on the porous spreading layer by coating and then drying the pulverized and respective alkali-denatured Exprotab to have the following coverage:

| | |
|---|---|
| Alkali-Denaturated Exprotab | 6 g/m² |
| Nonylphenoxypolyethoxyethanol (Containing 9 to 10 (average) of Oxyethylene Units) | 0.2 g/m² |

The thus formed laminates were contained, respectively, in a slide same as used in Example 5 to prepare slides 5, 6, 7 and 8 formed of multilayered immunoassay elements.

10 µl for each of a 10 µg/ml solution of the amlylase-anti-theophylline IgG conjugate synthesized in Synthesis Example 1 was spotted on each of the slides 5 to 8, which were maintained at 37° C. for 6 minutes for incubation, and then the optical density of the reflected light having a wavelength of 650 nm was measured from the PET support side to determine the optical density (A) of the reflected light.

Separately, 50 µl of a 10 µg/ml solution of the aforementioned enzyme-labelled antibody (i.e. amylase-anti-theophylline IgG conjugate) was mixed with 50 µl of a 20 µg/ml solution of the polymerized antigen (i.e. theophylline-BSA Conjugate) synthesized in Synthesis Example 2 to prepare a mixture. 10 µl of the mixure was spoted on each of the slides 5 to 8, incubated at 37° C. for 6 minutes, and then the optical density of the reflected light was measure to know the density (B). For each slide, the difference between the optical densities (A)–(B) was calculated. As clearly seen from the following Table 1, the presence of a polymerized antigen could be detected while using particles having average particle diameters ranging within 3 to 32 µm. It was found that the sensitivity (shown by (A)) became higher as the particle size was decreased, whereas the numerical value (B) corresponding to the background density was increased as the particle size became smaller. These results revealed that the more preferable particle size ranged within the particle diameter of 3 to 10 µm, and particularly preferably within the particle diameter of 5 to 10 µm.

TABLE 1

| Slide No. | 5 | 6 | 7 | 8 |
|---|---|---|---|---|
| Average Particle Diameter of Pulverized Particle (µm) | 3 | 5 | 10 | 32 |
| Optical Density of Reflected Light: | | | | |
| A | 1.152 | 1.092 | 0.550 | 0.160 |
| B | 0.560 | 0.240 | 0.120 | 0.090 |
| A–B | 0.592 | 0.852 | 0.430 | 0.070 |

What is claimed is:

1. An immunoassaying process for quantitatively analyzing an amount of a low molecular weight antigen in a sample by determining the change in enzymatic activity caused by competitive reactions between an enzyme-labelled antibody and said low molecular weight antigen and a conjugate of said low molecular weight antigen with a high molecular weight compound, comprising the steps of:

(a) mixing the sample containing the low molecular weight antigen, the enzyme-labelled antibody, and the conjugate of the antigen and the high molecular weight compound so as to allow the competitive reactions;

(b) applying a reaction product mixture of the competitive reactions of step (a) on a substrate layer containing a non-diffusible substrate for forming a diffusible material in the presence of said enzyme, said non-diffusible substrate being a pulverized insoluble polysaccharide which is classified after pulverization and has an average particle diameter of from 3 to 5 µm;

(c) allowing to migrate said diffusible material formed in said substrate layer into a reagent layer for detecting said diffusible material; and (d) measuring the amount of said diffusible material migrating into said reagent layer.

2. An immunoassaying process for quantitatively analyzing an amount of a macromolecular antigen in a sample by determining the change in enzymatic activity caused by a reaction between an enzyme-labelled antibody and said macromolecular antigen comprising the steps of:

(a) mixing the sample containing the macromolecular antigen and the enzyme-labelled antibody so as to allow the reaction;

(b) applying a reaction product mixture of the reaction of step (a) on a substrate layer containing a non-diffusible substrate for forming a diffusible material in the presence of said enzyme, said non-diffusible substrate being a pulverized insoluble polysaccharide which is classified after pulverization and has an average particle diameter of from 3 to 5 µm;

(c) allowing to migrate said diffusible material formed in said substrate layer into a reagent layer for detecting said diffusible material; and (d) measuring the amount of said diffusible material migrating into said reagent layer.

3. In an immunoassay element for quantitatively analyzing a low molecular weight antigen by determining the change in enzymatic activity caused by competitive reactions between an enzyme-labelled antibody and said low molecular weight antigen and a conjugate of said low molecular weight antigen with a high molecular weight compound, or a macromolecular antigen by determining the change in enzymatic activity caused by a reaction between an enzyme-labelled antibody and said macromolecular antigen, wherein said element comprises a substrate layer containing a non-diffusible substrate which forms a diffusible material in the presence of said enzyme and a reagent layer for detecting said diffusible material;

the improvement which comprises said non-diffusible substrate being a pulverized water-insoluble polysaccharide having an average particle diameter of from 3 to 10 μm.

4. The immunoassay element of claim 3, wherein said pulverized insoluble polysaccharide is carboxymethylated starch.

5. The immunoassay element of claim 3, wherein said pulverized insoluble polysaccharide is denaturated by an alkali or thermal treatment.

6. The immunoassay element of claim 4, wherein said carboxymethylated starch is denaturated by an alkali or thermal treatment.

7. The immunoassay element of claim 7, wherein said enzyme labelling to said antigen is a glucosidase.

8. The immunoassay element of claim 3, wherein said glucosidase is α-amylase.

9. The immunoassay element of claim 3, further comprising a fragmenting enzyme for fragmenting said diffusible material into a lower molecular weight product and contained in said reagent layer or another layer laminated under said reagent layer.

10. The immunoassay element of claim 9, further comprising a reagent composition for reacting with said lower molecular weight product to form a dye having an absorption peak in the visible wavelength range and contained in said reagent layer or another water-permeable layer.

11. The immunoassay element of claim 3, wherein said enzyme-lablelled antibody is contained in said substrate layer or another layer laminated on said substrate layer.

* * * * *